(12) United States Patent
Sarel

(10) Patent No.: US 6,949,073 B2
(45) Date of Patent: Sep. 27, 2005

(54) DYSPNEA MONITOR, AND TELEMEDICINE SYSTEM AND METHOD

(75) Inventor: Oded Sarel, Even Yehuda (IL)

(73) Assignee: Home-Medicine.com, Inc., Even Yehuda (IL)

( * ) Notice: Subject to any disclaimer, the term of this patent is extended or adjusted under 35 U.S.C. 154(b) by 196 days.

(21) Appl. No.: 10/262,874

(22) Filed: Oct. 3, 2002

(65) Prior Publication Data

US 2004/0068197 A1 Apr. 8, 2004

(51) Int. Cl.$^7$ .............................. A61B 5/08
(52) U.S. Cl. ................ 600/529; 600/300; 600/586
(58) Field of Search ................ 600/300–301, 600/529–543, 586; 73/23.3; 128/920, 200.24

(56) References Cited

U.S. PATENT DOCUMENTS

| | | | | |
|---|---|---|---|---|
| 4,351,344 A | * | 9/1982 | Stenzler | 600/533 |
| 5,165,417 A | * | 11/1992 | Murphy, Jr. | 600/529 |
| 5,619,991 A | | 4/1997 | Sloane | |
| 5,677,979 A | | 10/1997 | Squicciarini et al. | |
| 5,758,652 A | | 6/1998 | Nikolic | |
| 5,765,563 A | * | 6/1998 | Vander Schaaf | 600/538 |
| 5,769,074 A | | 6/1998 | Barnhill et al. | |
| 5,791,342 A | | 8/1998 | Woodard | |
| 5,791,908 A | | 8/1998 | Gillio | |
| 5,811,681 A | | 9/1998 | Braun et al. | |
| 5,827,180 A | | 10/1998 | Goodman | |
| 5,840,018 A | | 11/1998 | Michaeli | |
| 5,842,975 A | | 12/1998 | Illyes et al. | |
| 5,842,977 A | | 12/1998 | Lesho et al. | |
| 5,848,975 A | | 12/1998 | Phillips | |
| 5,865,733 A | | 2/1999 | Malinouskas et al. | |
| 5,868,134 A | | 2/1999 | Sugiyama et al. | |
| 5,868,135 A | | 2/1999 | Kaufman et al. | |
| 5,868,669 A | | 2/1999 | Iliff | |
| 5,873,369 A | | 2/1999 | Laniado et al. | |
| 5,892,570 A | | 4/1999 | Stevens | |
| 5,895,345 A | | 4/1999 | Knelson | |
| 5,897,493 A | | 4/1999 | Brown | |
| 5,902,234 A | | 5/1999 | Webb | |
| 5,906,208 A | | 5/1999 | Ishikawa et al. | |
| 5,907,291 A | | 5/1999 | Chen et al. | |
| 5,961,447 A | * | 10/1999 | Raviv et al. | 600/300 |
| 6,022,315 A | * | 2/2000 | Iliff | 600/300 |
| 6,168,568 B1 | * | 1/2001 | Gavriely | 600/529 |

FOREIGN PATENT DOCUMENTS

WO    WO 01/30231    5/2001

* cited by examiner

*Primary Examiner*—Robert L. Nasser
*Assistant Examiner*—Patricia Mallari

(57) ABSTRACT

Breathing interval measurement apparatus for measuring breathing of a subject, the apparatus comprising: a breathing interval beginning determinator, a breathing interval end determinator, and a timer associated with said breathing interval beginning determinator and said breathing interval end determinator to measure an interval between activation of said determinators, and a processor operable with said timer to assign levels of importance to said measured time interval.

52 Claims, 8 Drawing Sheets

Welcome to your online checkup
for 11/6/01

1. Login     Name    [          ]

Password [          ]

Fig. 9

Hello Mr Smith

Please answer the following questions

1. How do you feel today?

Fine ◎    OK ◎    Lousy ◎    Nauseous ◎    Terrible ◎

2. Have you taken this morning's tablets?

Yes     No

Fig. 10

ND TELEMEDICINE
DYSPNEA MONITOR, AND TELEMEDICINE SYSTEM AND METHOD

FIELD OF THE INVENTION

The present invention relates to a telemedicine system and method and a dyspnea monitor device and method for use therewith.

BACKGROUND OF THE INVENTION

A number of respiratory problems are preceded by detectable reductions in the ability to inhale or hold one's breath. Thus, it is possible to determine from a simple breathing test whether a patient is likely to suffer from such problems in the short term. Such a simple test is described in the literature in which the patient is placed in a rest position, asked to take a deep breath and then to count continuously until he has to take a breath again. An unusually short interval between breaths is indicative of congestion of the lungs or breathing passages.

The patient is generally not in the presence of a doctor at the times the test can yield the most helpful information, and indeed, the test is most useful as part of regular and frequent monitoring.

Furthermore the results of the test taken alone may not lead directly to any given diagnosis, the doctor preferring to take the test results in combination with other patient indicators before reaching a diagnosis of any kind.

Generally, automatic decision devices exist but are not widely used in the medical field since it is difficult to determine how decisions have been made and how different factors have been taken into account if at all.

An earlier patent application of the same inventor, WO IL00/00678, filed Oct. 25, 2000 describes a system in which a plurality of tests can be administered remotely over a telemedicine system, the patient being given instructions to administer the tests and then the test results being considered together to produce recommendations. The recommendations are then given either to the patient or to the doctor or both. A rule structure is used to lead from results to recommendations in a way that allows for easy checking by the responsible doctor and which avoids masking of bad test results by other better test results. The rule structure is however inadequate for certain given situations.

In the event that the same patient is being monitored by more than one doctor for different reasons or conditions, the above device requires either that the single monitoring device monitors everything and each doctor receives all of the information, or that two separate monitoring instances are used, increasing the inconvenience to the patient.

Earlier patents relating to telemedicine include: U.S. Pat. Nos. 5,907,291; 5,906,208; 5,902,234; 5,897,493; 5,895,354; 5,892,570; 5,879,292; 5,873,369; 5,868,669; 5,868,135; 5,868,134; 5,865,733; 5,855,550; 5,848,975; 5,842,977; 5,842,975; 5,840,018; 5,827,180; 5,811,681; 5,791,908; 5,791,342; 5,769,074; 5,758,652; 5,677,979; 5,619,991.

SUMMARY OF THE INVENTION

According to a first aspect of the present invention there is thus provided breathing interval measurement apparatus for measuring breathing of a subject, the apparatus comprising a breathing interval beginning determinator, a breathing interval end determinator, and a timer associated with said breathing interval beginning determinator and said breathing interval end determinator to measure an interval between activation of said determinators, and a processor operable with said timer to assign levels of importance to said measured time interval.

The apparatus preferably comprises an instruction unit for providing interactive instructions to said subject.

Preferably, said instruction unit is remotely located.

Preferably, said breathing interval end determinator comprises a sound analyzer operable to identify intake of breath.

Preferably, said sound analyzer is operable to make said determination from sound envelope measurement.

Preferably, said sound analyzer is operable to make said determination from identification of sounds indicative of breathing end.

Preferably, said breathing interval beginning determinator comprises a sound analyzer operable to identify intake of breath.

Preferably, said sound analyzer is operable to make said determination from sound envelope measurement.

Preferably, said sound analyzer is operable to make said determination from identification of sounds indicative of breathing start.

Preferably, said breathing interval beginning determinator comprises a sound analyzer operable to identify intake of breath.

Preferably, said breathing interval end determinator is operable to determine a breathing interval end over a remote connection.

Preferably, said breathing interval beginning determinator is a user activation unit.

Preferably, the processor is operable to assign high levels of importance to short measured intervals and successively lower levels of importance to successively longer intervals.

Preferably, said processor is operable to define at least four levels of importance to said result.

Preferably, the processor is operable to define at least seven levels of importance.

Preferably, said processor is remotely located.

Preferably, the processor is arranged to receive other measurements from said patient, and to assign levels of importance thereto, and comprising logic for combining said assigned levels of importance to form a recommendation.

Preferably, said processor further comprises a communicator for selecting at least one communication target and communicating said recommendation to said target.

Preferably, said target is said subject.

Preferably, said target comprises medical personnel.

Preferably, said target is selectable in accordance with said recommendation.

Preferably, given recommendations have a plurality of selectable targets.

Preferably, said plurality of selectable targets include at least one of a group comprising a laboratory for carrying out a respective test, a pharmaceutical supplier for supplying a relevant pharmaceutical, a hospital for making available medical facilities, a specialist medical practitioner for providing specialist medical services and a general medical practitioner for providing generalized medical services.

The apparatus preferably comprises target input functionality through which at least one of said medical personnel is able to select any of said measurements and recommendations to be automatically informed of.

Preferably, said communicator is operable to communicate messages of successively increasing levels of importance in accordance with said recommendation.

Preferably, said recommendations are associated with follow-up questions selected to test an understanding of said recommendations, the apparatus further comprising follow-up functionality operable to select at least one of said predetermined follow-up questions associated with said recommendation to communicate to said subject via said communicator, and an evaluator to evaluate a response of said subject, to said question, thereby to determine whether a subject has understood said recommendation.

The apparatus preferably comprises a telephone connection to connect between said subject and said processor.

Preferably, said breathing interval beginning determinator is a telephone key.

Preferably, said communicator is an audio communicator.

Preferably, said breathing interval end determinator is a telephone key.

The apparatus preferably comprises a telephone microphone for remotely sensing said breathing of said subject.

Preferably, said timer is remotely located from said subject.

The apparatus preferably comprises a memory for storing profiles of individual subjects, and wherein said processor comprises an identity matcher to obtain identity information of a subject and to associate said subject with a respective profile, thereby to modify said recommendation based on said respective profile.

The apparatus preferably comprises an interactive profile builder for interactively remotely asking questions of a subject and processing answers of a subject thereby to individualize a respective profile for said subject.

Preferably, said remote interactive profile builder comprises an Internet text-based form.

Preferably, said remote interactive profile builder is adapted to interact with said subject via mobile telephony.

Preferably, said remote interactive profile builder comprises voice processing.

Preferably, said remote interactive profile builder comprises voice processing.

The apparatus preferably comprises subject-operable language selection functionality to allow a subject to select a language for said interaction.

Preferably, said identity matcher comprises log-in functionality for interactively obtaining said identity information from said subject.

Preferably, said profile comprises medical history information of said subject, said logic for combining further being operable to combine said medical history with said measurements to adjust said levels of importance, thereby to modify said recommendation.

Preferably, said logic for combining includes predetermined modification rules for modifying said levels of importance in accordance with particular conditions appearing in said history.

Preferably, said particular conditions with predetermined modification rules include any one of a group comprising: CVA, brain hemorrhage, brain blockage, TIA, Diabetes, Bruit, and PMI, and a combination thereof.

Preferably, said measurements comprise blood pressure.

Preferably, each one of a plurality of conditions is assigned a predetermined delta for at least one respective measurement, said logic being operable to assign a level of importance calculated from an initial threshold set assigned to said measurement combined with a summation of each delta for each respective condition.

Preferably, each one of a plurality of conditions is assigned a predetermined delta for at least one respective measurement, said logic being operable to assign a level of importance calculated from an initial threshold set assigned to said measurement combined with a summation of each delta for each respective condition.

Preferably, said logic for combining is further operable to combine a recommendation with an additional measurement to make an additional recommendation.

Preferably, said logic for combining is operable to combine said recommendation and said additional recommendation to form a third recommendation.

Preferably, said logic for combining is operable to combine at least one of said recommendation, said additional recommendation and said third recommendation with an additional input to derive a fourth recommendation.

The apparatus is preferably operable to base a plurality of recommendations on substantially an identical measurement set.

According to a second aspect of the present invention there is provided a remote interactive patient assessment system, comprising:

an input for receiving subject identification data and measurements remotely from a subject, an identifier for using said identification data to associate a subject with a prestored subject profile, a thresholder for assigning thresholds to respective measurements from which to derive levels of importance of said measurements, said thresholder being operable with said subject profile to modify said thresholds in accordance with subject medical conditions found in said subject profile, and combination logic for combining said levels of importance to form a first recommendation.

Preferably, each one of a plurality of conditions is assigned a delta for application to each one of a plurality of measurements, said thresholder being adapted to apply a summation to each threshold of each delta for a respective measurement of each condition present in said profile.

Preferably, said thresholder is operable to define at least four levels of importance to said measurement.

Preferably, said thresholder is operable to define at least seven levels of importance.

The apparatus preferably comprises a communicator for selecting at least one communication target and communicating said recommendation to said target.

Preferably, said target is said subject.

Preferably, said target comprises medical personnel.

Preferably, said target is selectable in accordance with said recommendation.

Preferably, given recommendations have a plurality of selectable targets.

Preferably, said plurality of selectable targets includes at least one of a group comprising a laboratory for carrying out a respective test, a pharmaceutical supplier for supplying a relevant pharmaceutical, a hospital for making available medical facilities, a specialist medical practitioner for providing specialist medical services and a general medical practitioner for providing generalized medical services.

The apparatus preferably comprises target input functionality through which at least one of said medical personnel is able to select any of said measurements and recommendations to be automatically informed of.

Preferably, said communicator is operable to communicate messages of successively increasing levels of importance in accordance with said recommendation.

Preferably, said recommendations are associated with follow-up questions selected to test an understanding of said recommendations, the system further comprising follow-up functionality operable to select at least one of said predetermined follow-up questions associated with said recommendation to ask said subject, and an evaluator to evaluate a response of said subject, to said question, thereby to determine whether a subject has understood said recommendation.

Preferably, a telephone connection is used to connect with said subject.

Additionally or alternatively, said communicator is an audio communicator.

The apparatus preferably comprises an interactive profile builder for interactively remotely asking questions of a subject and processing answers of a subject thereby to individualize a respective profile for said subject.

Preferably, said remote interactive profile builder comprises an Internet text-based form.

Preferably, said remote interactive profile builder is adapted to interact with said subject via mobile telephony.

Preferably, said remote interactive profile builder comprises voice processing.

Preferably, said remote interactive profile builder comprises voice processing.

The system preferably comprises subject-operable language selection functionality to allow a subject to select a language for said interaction.

Preferably, said identifier comprises log-in functionality for interactively obtaining said identity information from said subject.

Preferably, said logic for combining includes predetermined modification rules for modifying said levels of importance in accordance with particular conditions appearing in said history.

Preferably, said particular conditions with predetermined modification rules including any one of a group comprising: CVA, brain hemorrhage, brain blockage, TIA, Diabetes, Bruit, and PMI, and a combination thereof.

Preferably, said measurements include blood pressure.

Preferably, said logic for combining is further operable to combine a recommendation with an additional measurement to make an additional recommendation.

Preferably, said logic for combining is operable to combine said recommendation and said additional recommendation to form a third recommendation.

Preferably, said logic for combining is operable to combine at least one of said recommendation, said additional recommendation and said third recommendation with an additional input to derive a fourth recommendation.

Preferably, the system is further operable to base a plurality of recommendations on substantially an identical measurement set.

According to a third aspect of the present invention there is provided a remote interactive patient assessment system, comprising:

an input for receiving subject identification data and measurements remotely from a subject, a thresholder for assigning thresholds to respective measurements from which to derive levels of importance of said measurements, combination logic for combining said levels of importance to form a first recommendation, and a communicator for communicating said recommendation to an output target, said communicator comprising a target selector for selecting at least one target for sending said recommendation.

Preferably, said target selector comprises target selection logic operable to select said at least one target according to a predefined target profile associated with said recommendation.

Preferably, said target selector comprises an interface for allowing a target to select data and measurements to be sent thereto.

Preferably, said targets include any one of a group comprising the subject, a pharmaceutical supplier, a specialist medical practitioner, a hospital, a general medical practitioner, and emergency medical services.

The system preferably comprises an identifier for obtaining identification information from a subject, thereby to associate said subject with a respective user profile.

Preferably, said user profile comprises any of a plurality of conditions in a subject's medical history, each one of said plurality of conditions being assigned a delta for application to each one of a plurality of measurements, said thresholder being adapted to apply a summation to each threshold of each delta for a respective measurement of each condition present in said profile.

Preferably, said thresholder is operable to define at least four levels of importance to said measurement.

Preferably, said thresholder is operable to define at least seven levels of importance.

The system preferably comprises a communicator for selecting at least one communication target and communicating said recommendation to said target.

Preferably, said communicator is operable to communicate messages of successively increasing levels of importance in accordance with said recommendation.

Preferably, said recommendations are associated with follow-up questions selected to test an understanding of said recommendations, the system further comprising follow-up functionality operable to select at least one of said predetermined follow-up questions associated with said recommendation to ask said subject, and an evaluator to evaluate a response of said subject, to said question, thereby to determine whether a subject has understood said recommendation.

The system preferably comprises a telephone connection to connect with said subject.

Additionally or alternatively, said communicator is an audio communicator.

The system preferably comprises an interactive profile builder for interactively remotely asking questions of a subject and processing answers of a subject thereby to individualize a respective profile for said subject.

Preferably, said remote interactive profile builder comprising an Internet text-based form.

Preferably, said remote interactive profile builder is adapted to interact with said subject via mobile telephony.

Preferably, said remote interactive profile builder comprising voice processing.

Preferably, said remote interactive profile builder comprising voice processing.

The system preferably comprises subject-operable language selection functionality to allow a subject to select a language for said interaction.

Preferably, said identifier comprises log-in functionality for interactively obtaining said identity information from said subject.

Preferably, said logic for combining includes predetermined modification rules for modifying said levels of importance in accordance with particular conditions appearing in said history.

Preferably, said particular conditions with predetermined modification rules include any one of a group comprising: CVA, brain hemorrhage, brain blockage, TIA, Diabetes, Bruit, and PMI, and a combination thereof.

Preferably, said measurements include blood pressure.

Preferably, said logic for combining is further operable to combine a recommendation with an additional measurement to make an additional recommendation.

Preferably, said logic for combining is operable to combine said recommendation and said additional recommendation to form a third recommendation.

Preferably, said logic for combining is operable to combine at least one of said recommendation, said additional recommendation and said third recommendation with an additional input to derive a fourth recommendation.

Preferably, the system is further operable to base a plurality of recommendations on substantially an identical measurement set.

According to a further aspect of the present invention there is provided a method of remotely monitoring breathing quality of a subject, comprising:

remotely determining that a breath has been begun by said subject, commencing a timing operation upon said determination, remotely automatically determining that said breath has been completed, ending said timing operation upon determination of said completion, comparing an output of said timing operation with at least one threshold, from said comparison making a determination of said breathing quality.

The method preferably comprises using sound envelope measurements to determine said beginning and said end of said breath.

The method preferably comprises using subject input to determine said beginning and using sound envelope measurements to determine said end.

The method preferably comprises using voice processing to determine said beginning and said end of said breath.

The method preferably comprises using subject input to determine said beginning of said breath and using voice processing to determine said end of said breath.

According to a further aspect of the present invention there is provided a method of automatic patient monitoring and assessment comprising:

receiving identity data of a subject, using said identity data to find a prestored subject profile comprising medical history of said subject including medical conditions of said subject, each condition having deltas associated therewith for modifying recommendation thresholds of given measurements, for each of said given measurements, modifying respective thresholds in accordance with a summation of each respective delta of each condition in said profile, receiving measurements from said subject corresponding to said given measurements, associating a status with each received measurement in accordance with said modified thresholds, and assessing said subject in accordance with said assigned statuses.

Preferably, said measurements and said thresholds correspond to a breathing test.

According to a further aspect of the present invention there is provided a method of automatic patient monitoring and assessment comprising:

receiving measurement data of a subject, using prestored thresholds to apply to each measurement a status, using combinational logic to derive output recommendations from said statuses, using predetermined recommendation profiles associated with each possible output recommendation to direct different output recommendations to different recipients in accordance with respective content of said output recommendation.

Preferably, said measurement data correspond to a breathing test.

According to a further aspect of the present invention there is provided a method of automatic patient monitoring and assessment comprising:

receiving measurement data of a subject, said data comprising a plurality of measurements, using prestored thresholds to apply to at least some of said measurements a respective status, using combinational logic to derive output recommendations from said respective statuses, receiving from potential recipients requests for output recommendations said recipient wishes to be informed of, and directing different output recommendations to different recipients in accordance with a respective recipient request.

Preferably, data corresponds to a breathing test.

In the present specification the terms "patient" and "subject" are used interchangeably. The term "patient" is taken to reflect the fact that the main use of the present embodiments is to provide ongoing monitoring in conjunction with medical treatment and thus the subject is generally a recipient of medical treatment. The term "subject" is a broader term and is used in recognition of the fact that the embodiments of the present invention are not restricted to recipients of medical treatment and may additionally be applied to healthy subjects of clinical trials and the like. In any case the terms, wherever they appear in the specification, are to regarded as synonymous.

BRIEF DESCRIPTION OF THE DRAWINGS

For a better understanding of the invention and to show how the same may be carried into effect, reference will now be made, purely by way of example, to the accompanying drawings, in which:

FIGS. 9, 10 and 11 are simplified diagrams showing possible user screens of a web implementation of the present invention, FIG. 9 showing a login page, FIG. 10 showing some introductory questions and FIG. 11 showing instructions for carrying out the breathing test of FIG. 1.

DESCRIPTION OF THE PREFERRED EMBODIMENTS

Figure 1:
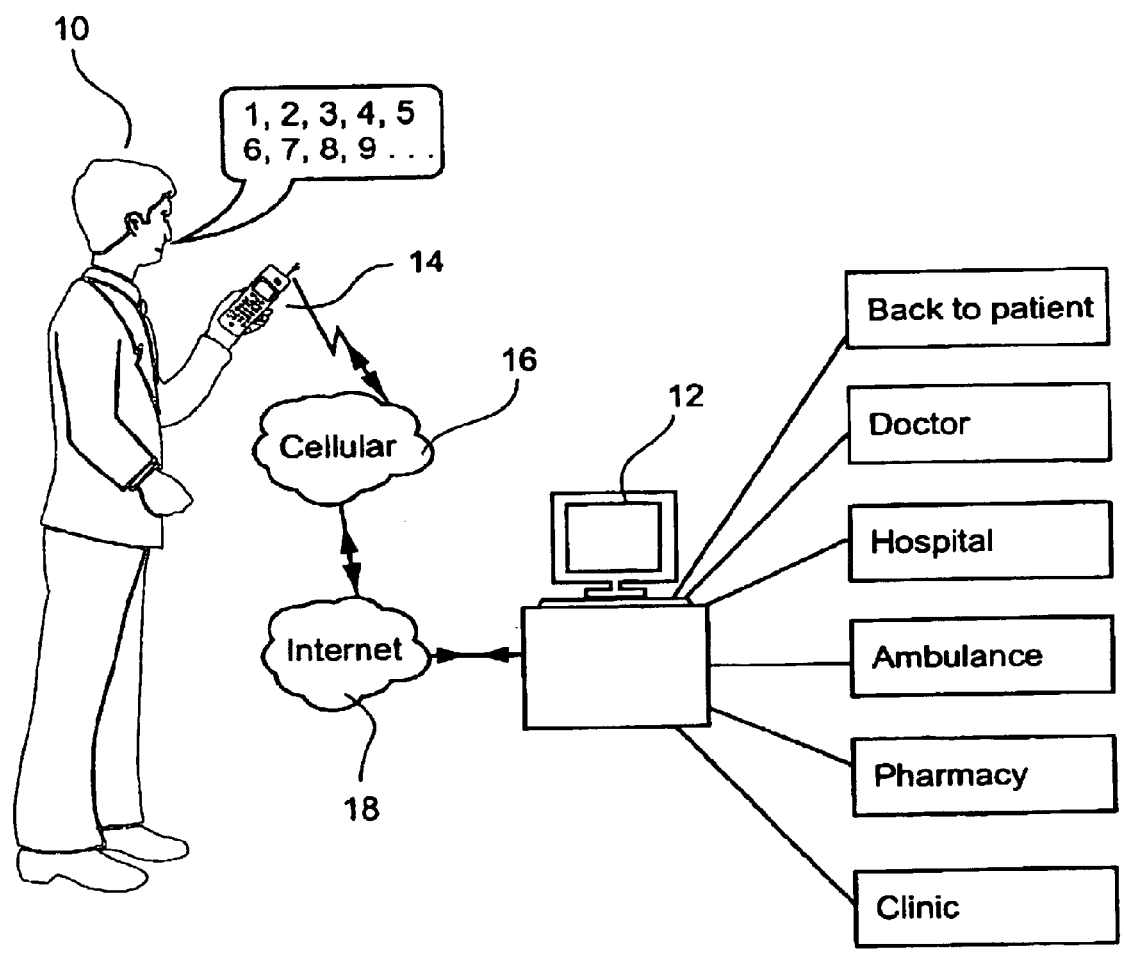
FIG. 1 is a simplified block diagram showing a subject undergoing breathing monitoring under control of a remote monitoring system according to a first embodiment of the present invention.

Reference is now made to FIG. 1, which is a simplified schematic diagram showing a first embodiment of the present invention. In the embodiment of FIG. 1 a patient or subject 10 contacts a remote monitoring unit 12 using a remote communication device such as a mobile telephone 14. It will be appreciated that any remote communication device may be considered including regular telephones, digital assistants, and Internet connected portable and other computers, and any available communication medium or network may be used, including the PSTN, cellular telephone networks, cable TV networks, and standard radio channels. Devices having some ability to allow digital communication are preferred for some embodiments of the present invention, and devices having a digital processing ability may provide some or all of the processing to be described hereinbelow of input measurements.

The remote communication device preferably connects to the monitoring unit 12 using any suitable network, for example the cellular network 16 and the Internet 18. It is stressed again that other alternatives include the PSTN, radio links, cable connections, and messaging services such as SMS.

The remote monitoring device 12 preferably asks the subject 10 to identify himself and then gives him instructions to carry out a particular monitoring or measurement procedure. The subject 10 is preferably told how to make the measurement and how to send the result to the monitoring unit 12.

In FIG. 1, the monitoring unit is denoted as a remote monitoring unit and is shown at the hospital side of the network connection. However, that is simply by way of example and the processing task carried out by the monitoring unit may be carried out at any convenient point between the patient and the medical professional. Typically, when the patient connects using a digital device the various processing tasks may be carried out at the user or split between the user and a remote unit. In other embodiments the user connects manually over a telephone, in which case processing is typically carried out remotely of the patient.

The monitoring unit preferably assesses the result, as will be explained in more detail below, to come to a recommendation or decision. The recommendation is then communicated either back to the patient, or to the doctor in charge of the treatment or to the hospital or to a pharmacy if a repeat prescription is needed, or to a clinic or, in the event of an emergency, the ambulance is contacted. Typical recommendations may be to stop treatment, change treatment, continue as before, see the doctor, go immediately to the hospital, etc.

In a preferred embodiment of the present invention the remote monitor 12 serves as a dyspnea monitor for monitoring the intervals of a subject's breathing, typically to ensure that he is not suffering from constrictions or pneumonia or fluid in the lung or other breathing constrictions. Such monitoring is useful in giving advance warning of given conditions to allow early treatment.

When in use as a dyspnea monitor the subject is requested to relax and then inhale. The subject is then asked to breath out slowly or to count or to speak normally and the remote monitor times the interval until the next intake of breath. The measurement may be taken once or several times and an average determined. The remote monitor 12 is able to assign a status or level of importance to the result, such as red, amber, green. The status may be communicated back to the patient or may be communicated to the doctor etc. or may be combined with other results, thereby to provide more comprehensive monitoring of the patient. As will be explained in more detail below, the result may be interpreted in the light of a patient's known medical history so that, for example, results that in most cases would elicit only a green status may be given a red or amber status in the light of the appearance of a given condition in the patient's medical history.

As an alternative to red, amber, green, a preferred embodiment uses the five states 0, 1, 2, alert and emergency. In this case, alert may be a state calling for a medical professional to visit the patient whereas emergency may be a state calling the patient to head immediately for casualty. Alternatively, an alert state may send an e-mail whereas an emergency state may send a voice alert.

It will be appreciated that, as well as being used in association with remote communication, the monitoring device may be used alone, either for later connection to remote communication or simply to report results directly to the patient.

Figure 2:
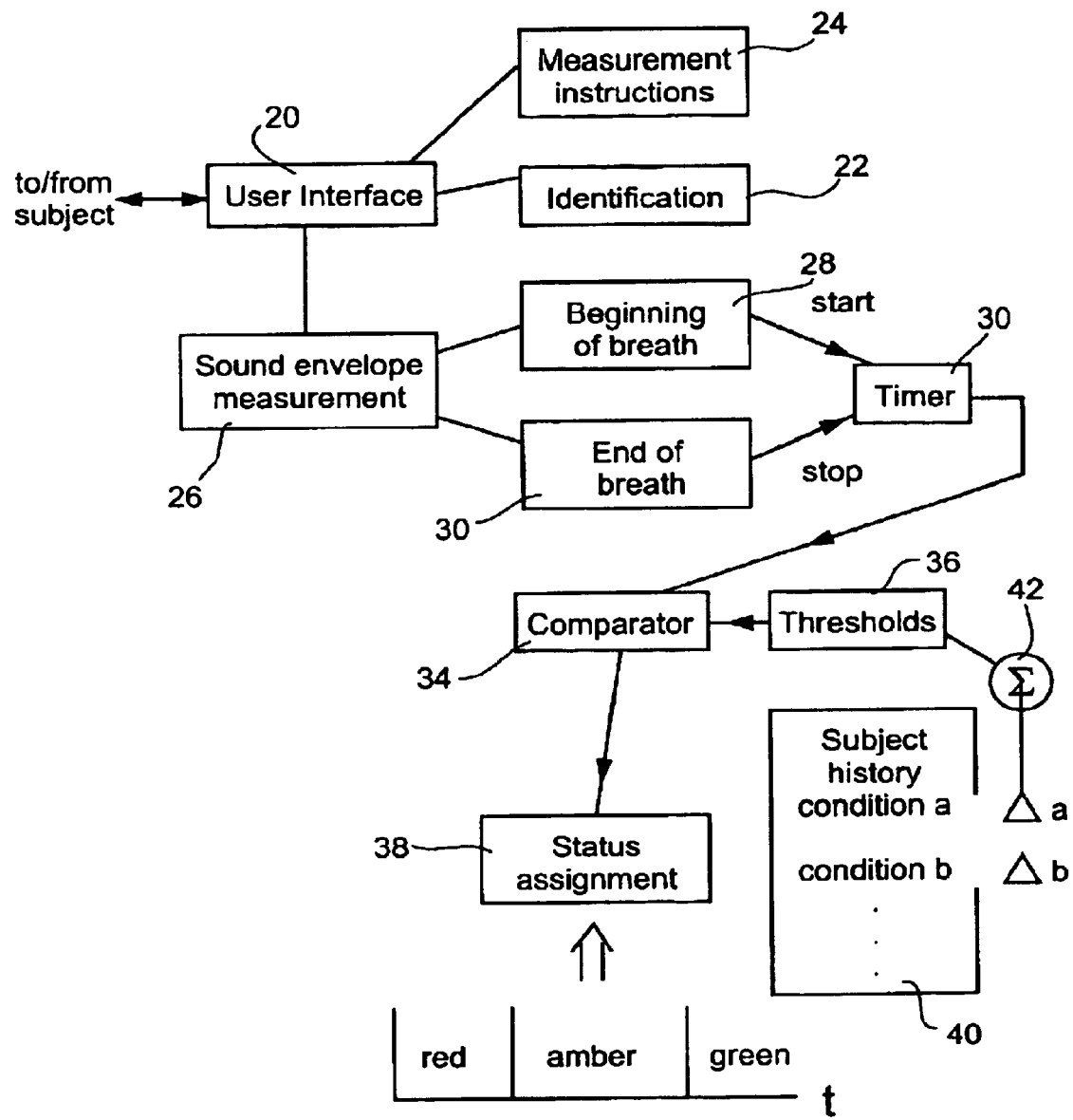
FIG. 2 is a simplified block diagram of the monitoring system of FIG. 1.

Reference is now made to FIG. 2, which is a simplified block diagram showing in more detail the monitoring apparatus of FIG. 1 configured as a dyspnea monitor, that is to say as a breathing interval measurement apparatus. The apparatus is useful for measuring breathing of a subject.

Remote monitor 12 comprises a user interface 20 for interfacing with the subject 10. The interface 20 is preferably designed to be suitable for the remote communication device being used by the user 10. That is to say if the remote communication device is a WAP-enabled mobile telephone then the interface preferably uses a WAP-compatible front end. If the remote communication device is an internet enabled desktop or mobile computer then the interface may for example make use of a web-page construction as a front end.

Preferably the user interface 20 allows the subject to enter an identification procedure 22. The identification procedure preferably asks the subject to give a name and perhaps a password. Identification is preferred for a number of reasons. First of all, as will be explained below, the subject may need to be associated with his own medical history in order to provide suitable decision making. Furthermore the results of the monitoring may need to be supplied to the doctor who is treating the particular subject. More generally the monitoring device is not intended as a freely available computerized doctor but rather as a tool to assist doctors in patient treatment. As such the addition of an identification procedure restricts use of the monitoring device to those patients whose doctors feel it will be beneficial and who are monitoring particular conditions and combinations of conditions.

An alternative identification procedure may make use of voiceprint or other personal identification technology.

In addition to the identification procedure the interface is also provided with sets of instructions 24 for advising the subject or patient on how to carry out given procedures. For example in the case of the dyspnea monitor, the user may be asked to sit down in a comfortable position and to relax. He is invited to indicate that he is relaxed by pressing on a given key. He is then asked to take a deep breath and begin counting. Suitable instruction sets may be made available for a wide variety of monitoring or measurement procedures and may be selected in accordance with a patient profile obtained following identification of the subject.

In the case of the dyspnea monitor the user preferably speaks a given sentence or counts or the like. The sentence is monitored, preferably at the remote monitoring unit 12, by a sound intensity envelope measurement unit 26. The sound intensity envelope measurement unit 26 produces a sound intensity envelope from which a beginning of exhalation may be identified by a breath beginning identifier 28. An output of the breath beginning identifier 28 is preferably used to trigger a timer 30 to start timing.

Likewise a second beginning of inhalation detector 32 is able to determine the end of the exhalation from the measured sound envelope. An output of the exhalation end detector is preferably used to stop the timer 30 so as to leave as an output of the timer an interval indicating the length of exhalation. The output may be used as it is or an average may be calculated from several measurements. The system may be set to ignore results in which exhalation was reduced in duration due to a subject coughing. On the other hand the system may be set to record such results as they may be of interest to the doctor.

Thus the output of the timer is either passed directly to a comparator 34 or the computed average or another statistical derivative of the timer output(s) is passed to the comparator 34. The comparator compares the result with a set of thresholds stored in a thresholder 36 and assigns a status or level of importance to the output at a status assigner 38, depending on where the result falls between the thresholds.

Preferably the identification procedure has allowed a subject profile 40 to be found. The subject profile preferably includes pertinent medical history of the subject including conditions that the subject is known to be suffering from. Generally speaking, the conditions that a user suffers from modify the levels of importance that should be attached to given measurements. For example a TB or an AIDS patient may require immediate treatment in the case of relatively minor restriction of the airways since such conditions are consistent with rapid development of airway constriction. A patient not suffering from the above conditions, on the other hand, may not require any kind of treatment at all when showing the same level of constriction. Other examples of patients requiring treatment include congestive heart failure and bronchial asthma.

Preferably, the above situation is dealt with by providing with each condition a set of deltas to be applied to the thresholds of individual measurements. Thus the TB condition may have a large delta to be applied to breathing interval thresholds, whereas it may have a smaller or zero delta for heart rate measurements. The AIDS condition may also have a large delta for breathing interval thresholds and preferably the device sums the different deltas of the conditions that are present in a summing unit 42 and moves the thresholds according to the summed output of the deltas. It will thus be appreciated that when a subject is suffering from both TB and AIDS, even a very slight change in exhalation time is liable to attain dire warnings from the system.

Status assignment is preferably made in a visually clearly understood manner, for example using the traffic light colors, red, amber and green. Additional states may be added, and existing states may be split into high and low states of the same color. Examples are high and low amber, high and low red, and a purple state. Visual clarity is helpful in allowing the doctor to understand easily how a given recommendation has been reached. Generally, prior art decision making systems have been rejected by the medical profession on the grounds that it has not been possible to investigate recommendations, for example to ensure that all factors have been taken into account. Reference numeral 44 refers to a graph showing measured exhalation time and showing a red region for the shortest breaths, an amber region for breaths of intermediate length and a green region for breaths of normal healthy length. Thus the monitor is operable to assign high levels of importance to short measured intervals and successively lower levels of importance to successively longer intervals.

In certain embodiments, the boundaries between the levels, initially the thresholds as prestored in thresholder 36, may be set universally, to be altered by the deltas of the patient's recorded conditions as described above. In other embodiments, the thresholds may be set by the doctor responsible for the given treatment in view of the patient's history without the option or the need for the modification by the deltas. In still other embodiments the doctor may set the thresholds on an individual basis but allow for modification by the deltas, either all deltas or only those of new conditions as they appear in the patient.

Likewise, deltas may be universally set for given conditions or may be set individually in the patient's medical profile.

In an alternative embodiment of the above, instead of using an automatic beginning of exhalation detector 28, the user is asked to press a key at the beginning of his exhalation, the press of the key being used to trigger the timer 30. In a further simplified embodiment the user is asked to press the same or another key in order to indicate the end of the exhalation, the second key press being used to stop the timer.

Figure 3:
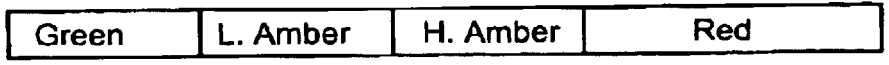
FIG. 3 is a simplified schematic diagram showing the division of a results space into status zones.

Reference is now made to FIG. 3, which is a simplified schematic diagram showing status zones that may be applied by the status assigner 38. In FIG. 3 a series of four zones are applied starting with green at one end, passing through low amber, high amber and red. Such a series of four status zones is applicable to examples similar to the dyspnea monitor in which one safe and one danger area are respectively located at either end of a result range.

Figure 4:
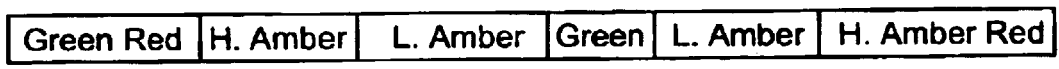
FIG. 4 is a simplified schematic diagram showing the division of a results space into a different arrangement of status zones.

Reference is now made to FIG. 4, which is an alternative embodiment to that of FIG. 3 of a zone distribution. In the example of FIG. 4 a safe zone is found towards the center of the range and danger zones to either side. The result range is thus divided into seven, red, high amber, low amber, green, low amber, high amber, red. A variation of the embodiment of FIG. 4, but less common, has a central red zone and green zones at either end.

It will be appreciated that numerous variations of the above could be used for zoning the results range. For example a single amber zone could be used or three or more different amber zones, or the red zone could be divided into a standard red zone and an emergency red zone.

Figure 5:
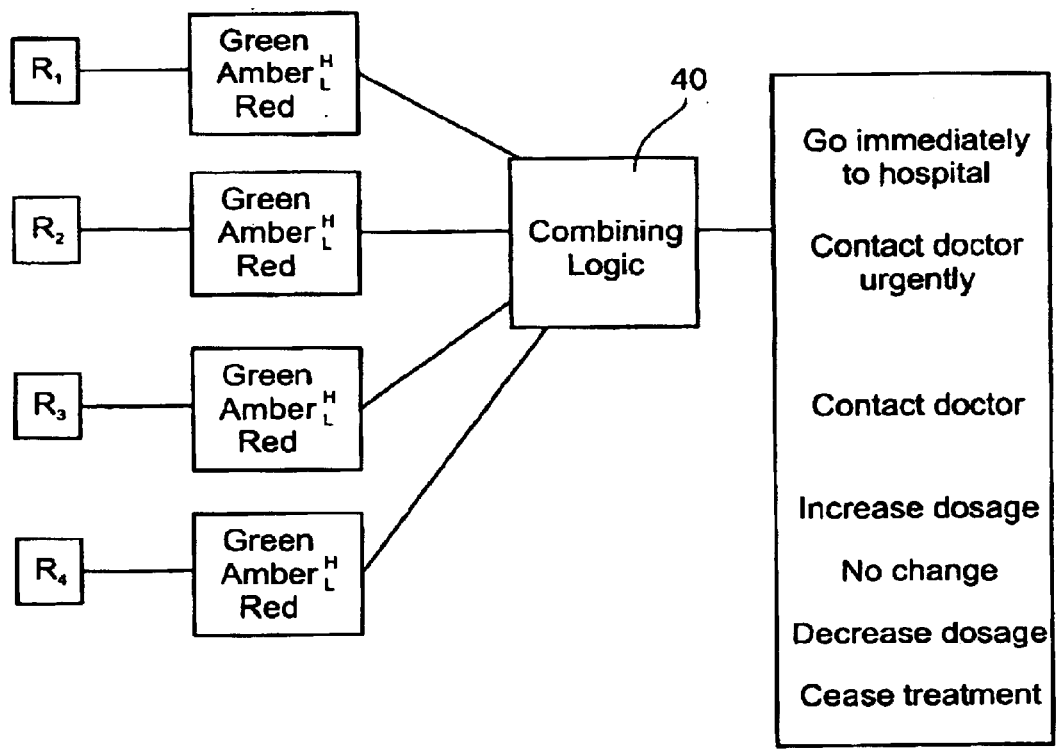
FIG. 5 is a simplified block diagram showing how a series of measurements may be combined into a set of decisions according to an embodiment of the present invention.

Reference is now made to FIG. 5, which is a simplified block diagram showing how a series of measurements from an individual subject may be considered by the present invention. In the embodiment of FIG. 5, a series of results R1 to R4 are obtained from the subject and each result is assigned a status in accordance with a predetermined zoning arrangement which may have been modified using deltas associated with conditions in the patient history, as described above. The output statuses of each of the four measurements are then fed into a combining logic unit 40. The different statuses are considered together to select one of a range 42 of possible output recommendations or decisions. The selection logic 40 preferably uses rules to associate the status combinations with the outputs, as opposed to weightings. A reason for using rules as opposed to weightings is that with weightings, a single bad result can be masked by other good results so that a serious condition may be missed. Using rules for matching allows such a situation to be avoided since a rule can be set to give the output "go directly to hospital" in response to the appearance of any red status in any of the measurements.

The output decisions or recommendations as shown in FIG. 5 may be directed toward the patient, which is to say the recommendation may be worded in layman's terms and sent to the patient as an output response following his submission of the measurements. Additionally or alternatively, however, as shown in FIG. 1, the results may be transferred to other parties, such as the doctor responsible for the patient's treatment. In certain circumstances, such as in post-operative monitoring, different doctors may be responsible for monitoring different problems. Thus it may be possible to direct monitoring results to the different parties as appropriate. For example all results and recommendations relevant to the patient's heart condition are directed to the responsible cardiologist whereas all results and recommendations relevant to the patient's asthmatic condition are directed to another doctor. All information regarding drug treatments is however preferably directed to both doctors.

It is further possible to direct output information on the basis of the recommendation content. For example, if the recommendation "increase dose" is issued, causing the patient to use his supply of pills faster, it may be useful to send a request for a repeat prescription to the pharmacist. Alternatively, in the event of the recommendation "go immediately to hospital" it may be useful to advise the hospital to make facilities available. For example, intensive care or operating facilities or particular surgical staff may be reserved in advance.

Other parties who may be usefully contacted at times may include a laboratory for carrying out a required test, a specialist medical practitioner for providing specialist medical services and a general medical practitioner for providing generalized medical services.

Preferably, interested parties such as the doctor involved in the treatment of the patient's asthma, are able to request the supply of specific data, and he may be able to specify the form in which he requires the data.

The system may be set to report, to the doctor, only messages of relatively high level importance, or alternatively to send to the doctor all output. In the case where the doctor is informed only of recommendations of high level importance, he may nevertheless be able to interrogate the system to obtain a full progress report.

A preferred embodiment of the present invention comprises a modification of the instruction unit 24 of the interface unit. In addition to the instructions for taking the relevant measurement a series of questions are supplied for ensuring that the patient has understood the instructions in the output recommendation. Thus a set of follow-up questions may be associated with each of the possible outputs, which set is selected in the event of the given recommendation being used. The questions are then put to the user, either orally in the case of an audio interface or in written form in the case of a text interface and the user's response is evaluated to determine whether the instructions have been understood. In the event that it appears that the instructions have not been understood the system may for example request medical personnel to contact the subject.

As mentioned above in respect of FIG. 2, user profiles are preferably used in order to take a subject's medical history into account in order to allow thresholds to be modified. The medical history may be input into the system by the subject's doctor or it may be obtained interactively from the patient. A preferred embodiment thus provides an interactive profile builder for interactively remotely asking questions of a subject and processing answers of a subject thereby to individualize a respective profile for the subject. A typical way of providing such an interactive profile builder may be as a web-based form. The form is preferably interactive in the sense that questions are arranged in branch format. Only if the subject answers in a certain way on a general question is the patient then asked more detailed questions on the same subject.

The profile builder is thus preferably an Internet text-based form, including an HTML form, an XML form, an STML form, a WAP form and a form based on any other suitable protocol or language. In an alternative embodiment the questions on the form may be spoken. In the event that voice processing is not of sufficient power to deal with spoken replies the subject may be asked to indicate different replies by pressing different keys on the keypad, for example in the event of the subject communicating via a non-digitally-enabled telephone. Whether using text or voice in the interface, there is preferably provided a facility for allowing the user to select the interface language.

In another preferred embodiment, instead of using deltas to alter thresholds in the event of given conditions, rules can be used, as with the combining logic 40 of FIG. 5.

Conditions to which deltas or predetermined modification rules may advantageously be applied include CVA, brain hemorrhage, brain blockage, TIA, Diabetes, Bruit, and PMI, and a combination thereof.

A particular measurement that the patient may be able to monitor at home using embodiments of the present invention is blood pressure. Threshold levels in blood pressure measurement would typically be levels that a doctor would wish to modify using deltas or otherwise in the presence of any of the above conditions.

Figure 6:
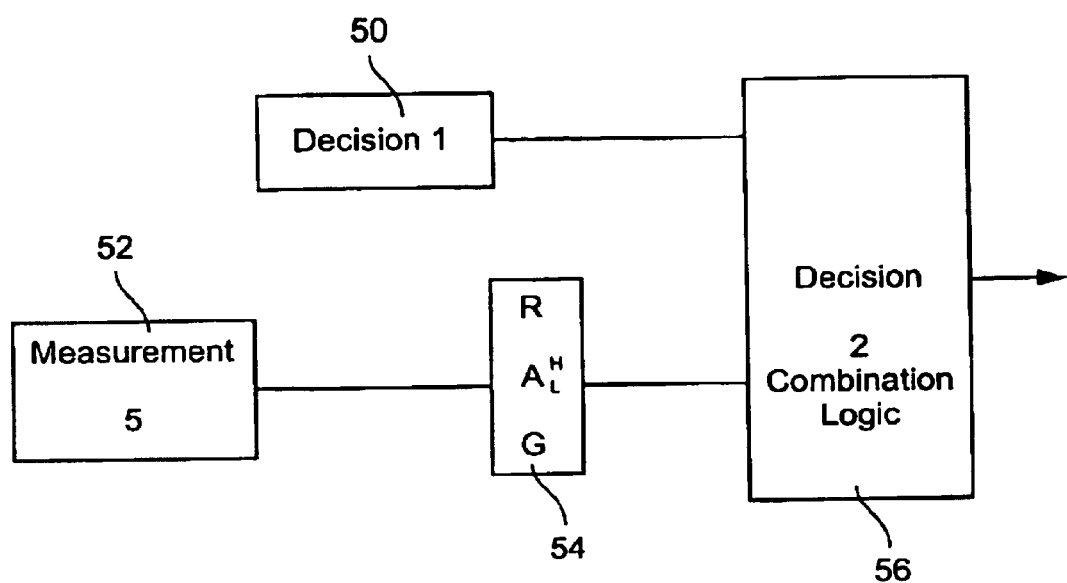
FIG. 6 is a simplified block diagram showing how a first decision may be combined with a new measurement to produce a further output.

Reference is now made to FIG. 6, which is a simplified block diagram showing a further embodiment of the present invention for making recommendations. In the embodiment of FIG. 6, a first recommendation 50 is reached as described in any of the ways described above. A further measurement 52 is then taken from the subject and a status is applied thereto, again as described above at a status assigner unit 54. The first recommendation 50 is then combined with the second measurement using second recommendation combination logic 56. The combination may be achieved by applying a status to the decision 1 output, that is to say regarding certain outputs as red, certain outputs as amber high and so on. Alternatively the combination logic 56 may relate to the individual recommendations themselves. For example a first recommendation to increase dosage combined with an amber high from the second measurement may lead to an overall recommendation "increase dosage plus contact doctor".

In one embodiment the arrangement of FIG. 6 provides a branched test arrangement. The subject is asked to carry out a general test and provides an answer. The result is then given a status. In the event of a red or high amber status a first recommendation is made which is to carry out a further test. The subject is then asked to carry out the further test and the result of the further test is used to make a further decision. For example the subject is initially asked about his overall feeling. If he replies that he feels OK then no tests are carried out. If he replies that he is feeling nauseous then the patient is asked to carry out one or more further tests.

It will be appreciated that a first recommendation can be combined with a single new measurement input or with a plurality of new measurement inputs. Conversely a single new measurement input may be combined with more than one existing recommendation to come to one or more secondary recommendations.

Additionally or alternatively, such a secondary recommendation may be combined with one or more further primary recommendations or one or more other secondary recommendations or one or more new inputs to arrive at a tertiary recommendation. In the same way, fourth, fifth and higher level recommendations may be made.

A branched structure of questioning is advantageous for conciseness. However branching of questions contains a bias towards a foreseen scenario. As an alternative to a branched structure, a further preferred embodiment of the present invention uses a series of lead questions aimed at establishing the presence of a range of conditions. Then instead of a branching structure, rule based logic is used to lead to appropriate follow-up questions. The lead questions and rule based structure may be more helpful than the tree based structure when for example monitoring for heart problems which unexpectedly develops into pneumonia.

Thus, in following a heart patient, the following parameters may be monitored, chest pain, ability to lie down, palpitation, blood pressure, heart rate, weight, and shortness of breath.

Now, if all the answers and the test results are within acceptable limits, except that the patient is showing signs of shortness of breath, then a rule may be set that when shortness of breath is inconsistent with the other results, the system is to start looking for other possibilities. The system may thus be set to ask for information regarding temperature, coughing, sputum (wet cough), whether someone in the family is or has recently been suffering from a respiratory disease or infectious lung disease. It may ask the patient if he is wheezing.

If the patient replies that he has a temperature (vital signs), rash (skin disorder), and arthralgia (skeletal problems), the system may be set via appropriate rules to raise questions about allergy to the current medication and the possibility may be raised of using a new medication.

Such questions may include whether the patient has had alergic reactions in the past. Is it the first occurrence of arthralgia? Is there any kind of redness or swelling in the joints. The system is preferably set to take sufficient questions to enable the forming of a view on the patient's condition.

An example of in which rule-based logic outdoes tree-based logic is as follows:

A patient has answered questions that lead to swelling of joints. Subsequently the patient indicates that are problems with urine. The combination of these two answers suggests possible spread of some kind of autoimmune disease, at which point it is appropriate to ask the patient whether his eyes are red, what is the state of his wisdom teeth, and whether there have been changes in the color of his excrement. He may be asked whether his joints feel particularly stuck first thing in the morning. A rule based structure is the best way to get from the initial two questions to the subsidiary questions in the above case simply because the follow-up questions are trivial issues when considering each of the first two questions in isolation, and therefore would be extremely low down on the tree structure for each. The follow-up questions are only of importance once the above answers to both of the initial questions are known in combination.

In a particularly preferred embodiment of the present invention, a tree based structure is used initially to ask questions about the condition being monitored. Then an additional set of lead questions is asked and used together with initial answers in rule based logic to determine whether anything unexpected is happening.

Returning to the heart patient, if the patient is able to supply good, meaning clear, answers to the above set of questions, then it is possible to proceed. If the answers are ambiguous then either a tree or a rule-based structure may be used to ask the original question in a different way, for example a question about stiffness of joints can be rephrased by asking if the patient has added, or felt the need to add, more pillows at night.

Figure 7:
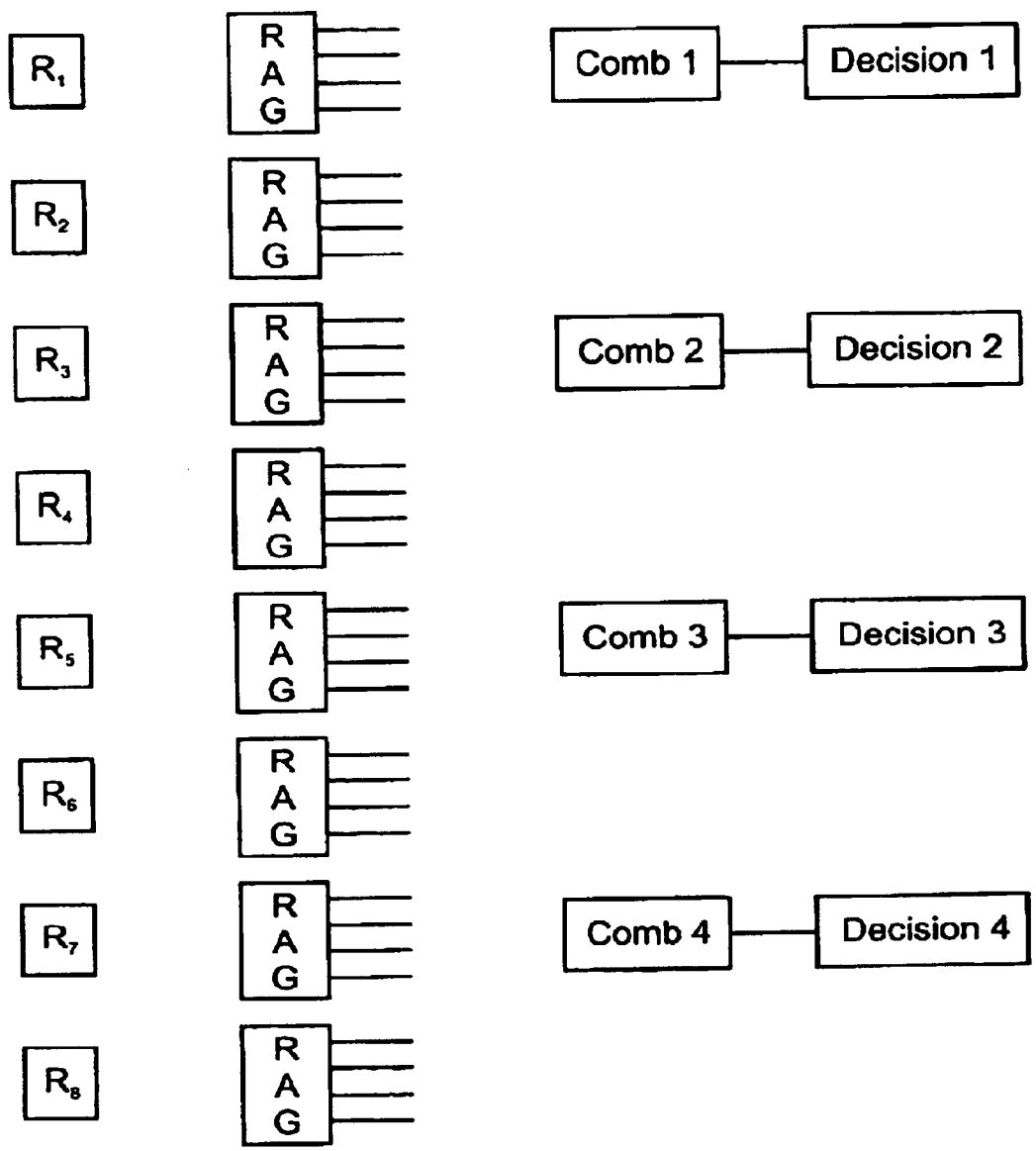
FIG. 7 is a simplified block diagram showing a single set of inputs being combined in different ways to lead to different decisions.

Reference is now made to FIG. 7, which is a simplified block diagram showing how a set of input measurements may each be combined in different ways using different combination logic and different rules to produce different output recommendations 1 to 4. In the figure, inputs R1 to R8 are each assigned status levels as before and then combined in four different sets of combination logic to yield different output recommendations. Thus a given set of measurements combined in different ways may lead to a series of different recommendations such that several different recommendations are based on substantially the same measurement set. Some of the output recommendations may use all of the inputs and some may use fewer than all of the inputs.

Figure 8:
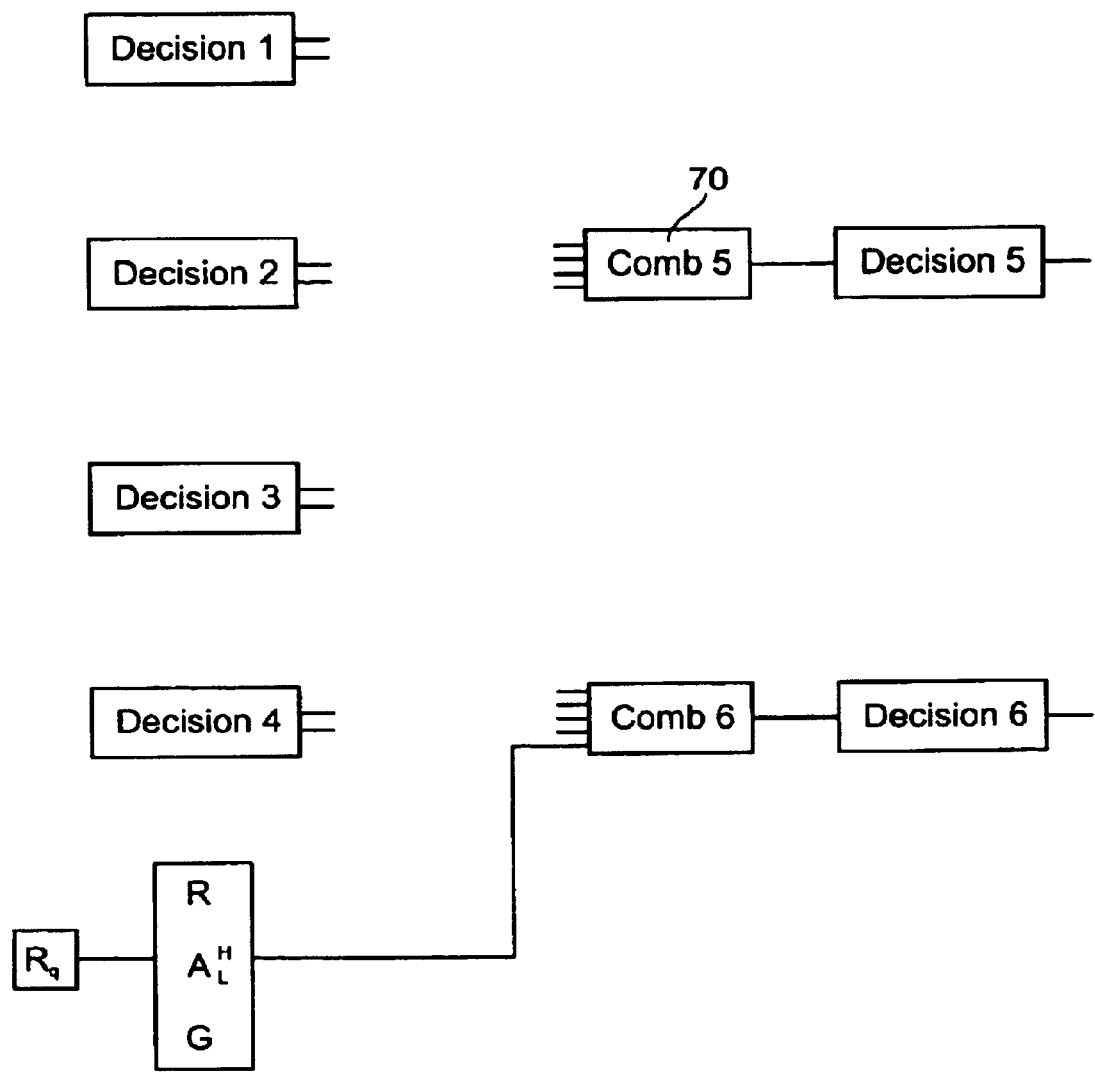
FIG. 8 is a simplified block diagram showing multiple first level decisions being combined to form a second level decision and also being combined with a new input to form another second level decision.

Reference is now made to FIG. 8, which is a simplified block diagram illustrating a layout for producing secondary recommendations. In FIG. 8, recommendations 1 to 4 of FIG. 7 are combined, using combination logic 70 to produce a secondary recommendation 5. Secondary recommendation 5 is thus produced, using rules, based on the combinations of recommendations 1 to 4. Recommendation 6 is produced by combination logic 72 using recommendations 1 to 4 and a new input R9.

Reference is now made to FIG. 9 which is a simplified schematic diagram showing a login screen for a web-browser implementation of the present invention. The user is simply asked to give his name and a password or pin number or the like in order to identify the patient and associate the patient with the correct profile.

Figure 11:
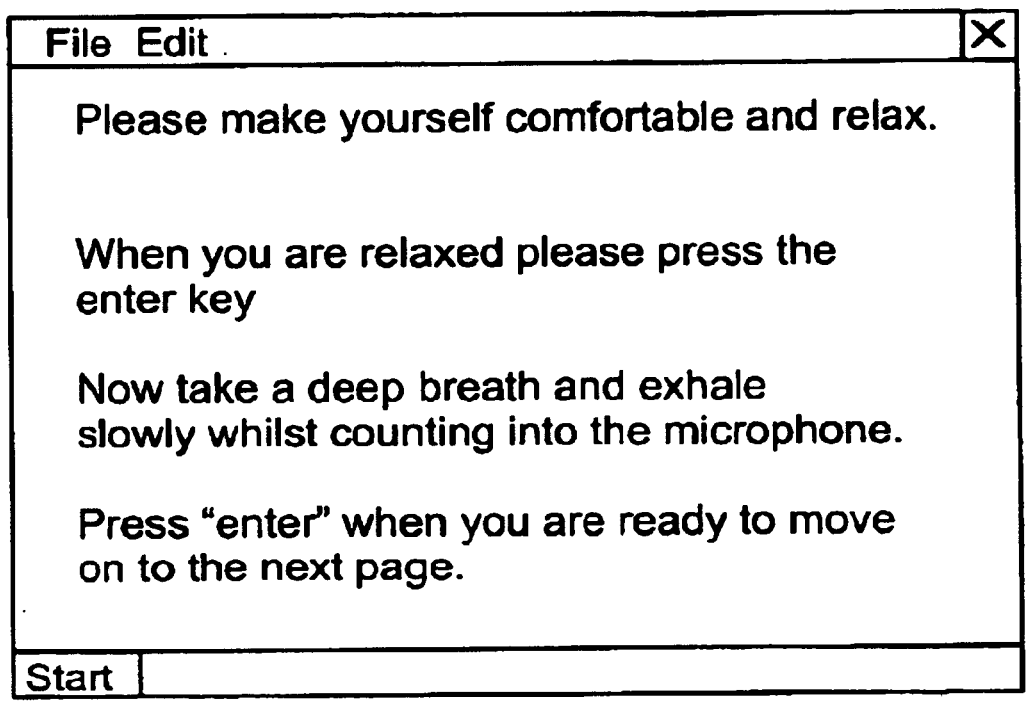

It is noted that whilst FIGS. 9–11 show connection over a web browser, the same information as carried by the web browser screens can be conveyed in voice form over a telephone connection, the patient making use of DTMF tones to provide his replies.

In either case a password is preferably used to assure the patient of confidentiality and to assure the doctor that the correct patient is answering. Preferably an alternative communication path is used to inform the patient of his password. Thus if the patient connects via a regular telephone, the password may be sent via beeper or mobile telephone.

Reference is now made to FIG. 10, which is a simplified schematic diagram showing an introductory screen, again for a web browser implementation of the present invention. The screen asks the user to answer some simple questions such as overall feeling and whether a patient has taken his pills.

Reference is now made to FIG. 11, which is a simplified diagram showing how the dyspnea monitoring test may be implemented in a web browser implementation of the present invention. The user is invited to relax and then take a deep breath. He is then asked to exhale slowly whilst counting into the microphone.

The interface 20, in the web implementation, may thus present to the subject a personalized web page which asks the subject questions relevant to his condition and is able to process the data in a way that is responsive to his current condition and to his case history. Any recommendation made is readily analyzable since inputs are coded in such a way as to be user friendly. Thus the system avoids the common criticism applied to expert systems of being black boxes and it being impossible to find out the reasons for the recommendation or to be sure that it has taken a given factor into account.

The monitoring arrangement of the above embodiments gives a patient an opportunity to answer routine questions before going to see a doctor. Particularly in the case of specialist doctors it can be advantageous for the doctor to have an idea of the situation or a status update before seeing the patient. Thus a patient who has been using an embodiment of the present invention for regular tests etc may receive a telephone call or an additional web form to answer routine questions before seeing the doctor.

Routine monitoring of the kind described hereinabove is particularly useful in cases of chronic illness, and for post-encounter or post operation follow-up, also after an invasive test or examination, or following chemotherapy, or giving birth. The system is useful in warning about post-hospitalization infection or relapses or impending bouts of pneumonia. In particular, one of the reasons that pneumonia is so often fatal is that it is often diagnosed too late for drug treatments to be effective.

The system may be used prior to an operation to provide to the patient an interactive pre-operation questionnaire which may be used to build a user profile as described above. The profile may then be used as described above to modify thresholds.

Again, as described above, questions may be arranged in a tree and branch format so that in the pre-encounter or pre-operation questionnaire, only sub-questions that appear to be relevant based on earlier questions are asked. Following the operation or encounter, a post encounter questionnaire may then be built up by branching in accordance with answers given in the pre-operation questionnaire.

In use, the present embodiments are preferably arranged so that telephone call charges are clearly distinguishable as being related to medical care. The calls are preferably charged to the hospital account or are routed through a specific exchange that takes only calls relating to patient monitoring so that it is intrinsically clear that all calls routed through the exchange are patient care related calls.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

What is claimed is:

1. Breathing interval measurement apparatus for measuring breathing of a subject, the apparatus comprising
   a breathing interval beginning determinator for using sound detection to determine a start of breath sound,
   breathing interval end determinator for using sound detection to determine an end of breath sound,
   a timer associated with said breathing interval beginning determinator and said breathing interval end determinator to measure an interval between activation of said determinators, said interval being a breathing length between a start and an end of breathing,
   a processor operable with said timer to assign levels of importance to said measured time interval,
   storage for storing a previous measurement, and
   a comparator for comparing said interval with said previous measurement.

2. Breathing interval measurement apparatus according to claim 1, further operable to base a plurality of recommendations on substantially an identical measurement set.

3. Breathing interval measuring apparatus according to claim 1, further comprising a communication unit for sending processed data of said breathing measuring to a remote location.

4. Breathing interval measuring apparatus according to claim 1, further comprising an instruction unit for providing interactive instructions to said subject.

5. Breathing interval measuring apparatus according to claim 4, wherein said instruction unit is remotely located.

6. Breathing interval measurement apparatus according to claim 1, wherein said breathing interval end determinator comprises a sound analyzer operable to identify intake of breath.

7. Breathing interval measurement apparatus according to claim 6, wherein said sound analyzer is operable to make said determination from sound envelope measurement.

8. Breathing interval measurement apparatus according to claim 6, wherein said sound analyzer is operable to make said determination from identification of sounds indicative of breathing end.

9. Breathing interval measurement apparatus according to claim 1, wherein said breathing interval beginning determinator comprises a sound analyzer operable to identify intake of breath.

10. Breathing interval measurement apparatus according to claim 9, wherein said sound analyzer is operable to make said determination from sound envelope measurement.

11. Breathing interval measurement apparatus according to claim 9, wherein said sound analyzer is operable to make said determination from identification of sounds indicative of breathing start.

12. Breathing interval measurement apparatus according to claim 6, wherein said breathing interval beginning determinator comprises a sound analyzer operable to identify intake of breath.

13. Breathing interval measurement apparatus according to claim 6, wherein said breathing interval end determinator is operable to determine a breathing interval end over a remote connection.

14. Breathing interval measurement apparatus according to claim 1, wherein said breathing interval beginning determinator is a user activation unit.

15. Breathing interval measurement apparatus according to claim 1, said processor being operable to assign high levels of importance to short measured intervals and successively lower levels of importance to successively longer intervals.

16. Breathing interval measurement apparatus according to claim 15, said processor operable to define at least four levels of importance to said result.

17. Breathing interval measurement apparatus according to claim 15, said processor operable to define at least seven levels of importance.

18. Breathing interval measurement apparatus according to claim 1, wherein said processor is remotely located.

19. Breathing interval measurement apparatus according to claim 17, wherein said processor is remotely located.

20. Breathing interval measurement apparatus according to claim 19, said processor being arranged to receive other measurements from said patient, and to assign levels of importance thereto, and comprising logic for combining said assigned levels of importance to form a recommendation.

21. Breathing interval measurement apparatus according to claim 20, wherein said processor further comprises a communicator for selecting at least one communication target and communicating said recommendation to said target.

22. Breathing interval measurement apparatus according to claim 21 wherein said target is said subject.

23. Breathing interval measurement apparatus according to claim 21, wherein said target comprises medical personnel.

24. Breathing interval measurement apparatus according to claim 23, wherein said target is selectable in accordance with said recommendation.

25. Breathing interval measurement apparatus according to claim 24, wherein given recommendations have a plurality of selectable targets.

26. Breathing interval measurement apparatus according to claim 25, wherein said plurality of selectable targets include at least one of a group comprising a laboratory for carrying out a respective test, a pharmaceutical supplier for supplying a relevant pharmaceutical, a hospital for making available medical facilities, a specialist medical practitioner for providing specialist medical services and a general medical practitioner for providing generalized medical services.

27. Breathing interval measurement apparatus according to claim 23, further comprising target input functionality through which at least one of said medical personnel is able to select any of said measurements and recommendations to be automatically informed of.

28. Breathing interval measurement apparatus according to claim 22, wherein said communicator is operable to communicate messages of successively increasing levels of importance in accordance with said recommendation.

29. Breathing interval measurement apparatus according to claim 28, wherein said recommendations are associated with follow-up questions selected to test an understanding of said recommendations, the apparatus further comprising follow-up functionality operable to select at least one of said predetermined follow-up questions associated with said recommendation to communicate to said subject via said communicator, and an evaluator to evaluate a response of said subject, to said question, thereby to determine whether a subject has understood said recommendation.

30. Breathing interval measurement apparatus according to claim 29, further comprising a telephone connection to connect between said subject and said processor.

31. Breathing interval measurement apparatus according to claim 30, wherein said breathing interval beginning determinator is a telephone key.

32. Breathing interval measurement apparatus according to claim 31, wherein said communicator is an audio communicator.

33. Breathing interval measurement apparatus according to claim 32, wherein said breathing interval end determinator is a telephone key.

34. Breathing interval measurement apparatus according to claim 33, comprising a telephone microphone for remotely sensing said breathing of said subject.

35. Breathing interval measurement apparatus according to claim 1, wherein said timer is remotely located from said subject.

36. Breathing interval measurement apparatus according to claim 35, further comprising a memory for storing profiles of individual subjects, and wherein said processor comprises an identity matcher to obtain identity information of a subject and to associate said subject with a respective profile, thereby to modify a recommendation based on said respective profile.

37. Breathing interval measurement apparatus according to claim 36, further comprising an interactive profile builder for interactively remotely asking questions of a subject and processing answers of a subject thereby to individualize a respective profile for said subject.

38. Breathing interval measurement apparatus according to claim 37, wherein said remote interactive profile builder comprises an Internet text-based form.

39. Breathing interval measurement apparatus according to claim 38, wherein said remote interactive profile builder is adapted to interact with said subject via mobile telephony.

40. Breathing interval measurement apparatus according to claim 37, wherein said remote interactive profile builder comprises voice processing.

41. Breathing interval measurement apparatus according to claim 39, wherein said remote interactive profile builder comprises voice processing.

42. Breathing interval measurement apparatus according to claim 37, comprising subject-operable language selection functionality to allow a subject to select a language for said interaction.

43. Breathing interval measurement apparatus according to claim 36, wherein said identity matcher comprises log-in functionality for interactively obtaining said identity information from said subject.

44. Breathing interval measurement apparatus according to claim 36, wherein each of said profiles comprises medical history information of a respective subject, said logic for combining further being operable to combine said medical history with measurements made by the timer to adjust said levels of importance, thereby to modify said recommendation.

45. Breathing interval measurement apparatus according to claim 44, wherein said logic for combining includes predetermined modification rules for modifying said levels of importance in accordance with particular conditions appearing in said history.

46. Breathing interval measurement apparatus according to claim 45, wherein said particular conditions with predetermined modification rules include any one of a group comprising: CVA, brain hemorrhage, brain blockage, TIA, Diabetes, Bruit, and PMI; and a combination thereof.

47. Breathing interval measurement apparatus according to claim 46, wherein said measurements comprise blood pressure.

48. Breathing interval measurement apparatus according to claim 45, wherein each one of a plurality of conditions is assigned a predetermined delta for at least one respective measurement, said logic being operable to assign a level of importance calculated from an initial threshold set assigned to said measurement combined with a summation of each delta for each respective condition.

49. Breathing interval measurement apparatus according to claim 47, wherein each one of a plurality of conditions is assigned a predetermined delta for at least one respective measurement, said logic being operable to assign a level of importance calculated from an initial threshold set assigned to said measurement combined with a summation of each delta for each respective condition.

50. Breathing interval measurement apparatus according to claim 48, wherein said logic for combining is further operable to combine a recommendation with an additional measurement to make an additional recommendation.

51. Breathing interval measurement apparatus according to claim 50, wherein said logic for combining is operable to combine said recommendation and said additional recommendation to form a third recommendation.

52. Breathing interval measurement apparatus according to claim 51, wherein said logic for combining is operable to combine at least one of said recommendation, said additional recommendation and said third recommendation with an additional input to derive a fourth recommendation.

\* \* \* \* \*